United States Patent
Hantash (10) Patent No.: US 12,251,402 B2
(45) Date of Patent: Mar. 18, 2025

(54) MESENCHYMAL STEM CELLS WITH ENHANCED IMMUNOSUPPRESSIVE CAPABILITY

(71) Applicant: Escape Therapeutics, Inc., San Jose, CA (US)

(72) Inventor: Basil M. Hantash, East Palo Alto, CA (US)

(73) Assignee: Escape Therapeutics, Inc., Turlock, CA (US)

( * ) Notice: Subject to any disclaimer, the term of this patent is extended or adjusted under 35 U.S.C. 154(b) by 42 days.

(21) Appl. No.: 16/750,554

(22) Filed: Jan. 23, 2020

(65) Prior Publication Data

US 2020/0155610 A1    May 21, 2020

Related U.S. Application Data

(62) Division of application No. 15/250,441, filed on Aug. 29, 2016, now Pat. No. 10,576,105.

(60) Provisional application No. 62/213,748, filed on Sep. 3, 2015.

(51) Int. Cl.
```
A61K 35/28    (2015.01)
A61K 9/00     (2006.01)
A61K 35/12    (2015.01)
C12N 5/0775   (2010.01)
```
(52) U.S. Cl.
CPC ............ *A61K 35/28* (2013.01); *A61K 9/0019* (2013.01); *C12N 5/0663* (2013.01); *C12N 5/0667* (2013.01); *A61K 2035/124* (2013.01); *C12N 2501/70* (2013.01)

(58) Field of Classification Search
CPC .................. A61K 35/28; A61K 9/0019; A61K 2035/124; C12N 5/0663; C12N 5/0667; C12N 2501/70
USPC ....................................................... 424/93.7
See application file for complete search history.

(56) References Cited

U.S. PATENT DOCUMENTS

| | | | |
|---|---|---|---|
| 7,601,699 B2 * | 10/2009 | Eilertsen ............ | C12N 15/1137 435/325 |
| 2010/0055785 A1 | 3/2010 | Hantash | |
| 2010/0173414 A1 | 7/2010 | Turovets et al. | |
| 2017/0065639 A1 | 3/2017 | Hantash | |

OTHER PUBLICATIONS

Kim et al., New Strategies for Overcoming Limitations of Mesenchymal Stem Cell-Based Immune Modulation, International Journal of Stem Cells vol. 8, No. 1, (May 2015), pp. 54-68.*

Aggarwal & Pittenger, Human Mesenchymal Stem Cells Modulate Allogenic Immune Cell Responses, Blood, 105 (4), 1815-1822, Feb. 15, 2005, (8 pages).
Beck and Trowsdale, "The Human Major Histocompatibility Complex: Lessons From the DNA Sequence," Annual Review of Genomics and Human Genetics, vol. 1, pp. 117-137, Sep. 2000.
Cirulli, et al., "The Class I HLA Reprtoire of Pancreatic Islets Comprises the Nonclassical Class Ib Antigen HLA-G," May 2006, Diabetes 55, 5, 1214-1222 (9 pages).
Fujimura, et al, "Neural differentiation of adipose-derived stem cells isolated from GFP transgenic mice," Biochemical and Biophysical Research Communications, vol. 333, Issue 1, Jul. 22, 2005, pp. 116-121.
Giuliani, et al., "Long-Lasting Inhibitory Effects of Fetal Liver Mesenchymal Stem Cells on T-Lymphocyte Proliferation," PLoS One 6(5): e19988. doi:10.1371/journal.pone.0019988, May 19, 2011, (10 pages).
Gronthos, S., et al., "Surface protein characterization of human adipose tissue-derived stromal cells," J. Cell. Physiol., 2001, 189: 54-63. doi:10.1002/jcp.1138.
Guo, et al., "Effects of 5-aza-2'-deoxycytidine on proliferation, differentiation and p15/INK4b regulation of human hematopoietic progenitor cells," Leukemia, 2006, vol. 20, pp. 115-121 (7 pages).
Hviid, et al., "HLA-G Polymorphisms and HLA-G Expression in Sarcoidosis," Mar. 2006, Sarcoidosis Vase Diffuse Lung Dis., 23, 1, 30-37.
Hviid, et al., "Polymorphism in the 5' upstream regulatory and 3' untranslated regions of the HLA-G gene in relation to soluble HLA-G and IL-10 expression," Jan.-Feb. 2006, Hum. Immunol. 67, (1-2), 53-62.
Ishitani, et al., "Alternative splicing of HLA-G transcripts yields proteins with primary structures resembling both class I and class II antigens," May 1992, Proc. Natl. Acad. Sci USA, 89, (9), 3947-3951(5 pages).
Polakova, et al., "Demethylating Agent 5-aza-2'-deoxycytidine Activates HLA-G Expression in Human Leukemia Cell Lines," Leukemia Research, 33 (2009), pp. 518-524 (7 pages).
Pook, et al., "Characterization of an expressible nonclassical class I HLA gene," Oct. 1991, Hum. Immunol. 32, (2), 102-109.
Rhodes and Trowsdale, "Genetics and Molecular Genetics of the MHC," Rev. Immunogenet, 1999, 1,(1): pp. 21-31.
Robinson and Marsh, "The IMGT/HLA Sequence Database," Reviews in Immunogenetics (2000), 2 (4), pp. 518-531.
Simmons, et al., "Isolation, Characterization, and Functional Activity of Human Marrow Stromal Progenitors in Hemopoiesis," Prog. Clin. Biol. Res. 389, 271-280, 1994.
Sua'rez-Alvarez et al. (2010) Epigenetic Mechanisms Regulate MHC and Antigen Processing Molecules in Human Embryonic and Induced Pluripotent Stem Cells. PLoS One 5(4): e10192. doi:10.1371/journal.pone.0010192.
Takele Teklemariam, et al., "Inhibition of DNA methylation enhances HLA-G expression in human mesenchymal stem cells," Biochemical and Biophysical Research Communications, 452, 753-759, 2014 (7 pages).

(Continued)

*Primary Examiner* — Jennifer M. H. Tichy
(74) *Attorney, Agent, or Firm* — Wilmer Cutler Pickering Hale and Dorr LLP (57) ABSTRACT

Compositions of HLA-G+ MSC and methods of using them, including methods of transplanting compositions of HLA-G+ MSC into human recipients, are provided. Also provided are methods of preparing compositions of HLA-G+ MSC, including by treatment with DNA methylation inhibitors.

13 Claims, 5 Drawing Sheets

(56) References Cited

OTHER PUBLICATIONS

Trowsdale, "Genomic Structure and Function in the MHC," Trends in Genetics, Apr. 1, 1993, 9 (4): pp. 117-122.
Yan, et al, "Induction of HA-G Expression in a Melanoma Cell Line OCM-1A Following the Treatment with 5-aza-2'-deoxycytidine," Cell Research, 15 (7): pp. 523-531, Jul. 2005 (9 pages).
Yie, et al., "Progesterone regulates HLA-G gene expression through a novel progesterone response element," Hum Reprod., Oct. 2006, 21 (10): pp. 2538-2544.
Zemmour, et al., "HLA Class I Nucleotide Sequences," Hum. Immunol. Jul. 1991, 31 (3): pp. 195-206.
Zuk, et al., "Human Adipose Tissue Is A Source of Multipotent Stem Cells," Molecular Biology of the Cell, vol. 13, pp. 4279-4295, Dec. 2002 (17 pages).

* cited by examiner

MESENCHYMAL STEM CELLS WITH ENHANCED IMMUNOSUPPRESSIVE CAPABILITY

RELATED APPLICATIONS AND INCORPORATION BY REFERENCE

This application is a divisional of U.S. patent application Ser. No. 15/250,441 filed Aug. 29, 2016, which claims the benefit of U.S. Provisional Application No. 62/213,748, filed on Sep. 3, 2015, the contents of which are incorporated herein by reference in their entirety.

The present application is also related to the disclosure in Takele Teklemariam, et al., *Inhibition of DNA methylation enhances HLA-G expression in human mesenchymal stem cells*, Biochemical and Biophysical Research Communications, 452, 753-759 (2014), available online on Sep. 6, 2014, the content of which is hereby incorporated by reference herein in its entirety. All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described herein.

FIELD

This invention generally relates to methods and compositions of mesenchymal stem cells, as well as to methods for using such cells, for example, to prevent or treat various injuries, diseases, and disorders in human and non-human animals.

BACKGROUND OF THE INVENTION

Mesenchymal stem cells (MSCs) are self-renewing multipotent cells capable of differentiating into several cell lineages including osteoblasts, chondrocytes, and adipocytes. MSCs have successfully been isolated from bone marrow, adipose, peripheral blood, umbilical cord blood and matrix, fetal blood and liver, connective tissue of dermis, and skeletal muscle sources.

The multi-differentiation potential of MSC raises a clinical interest to employ these cells for regeneration purposes, for example, in osteogenesis imperfecta. MSCs exhibit an immunomodulatory potential and have been shown to inhibit T and NK cell proliferation in vitro. Because of their immunosuppressive, self-renewal, and multi-lineage differentiation properties, MSCs have been used in human clinical trials for treatment of graft-versus-host disease, multiple sclerosis, and spinal cord injury. Since the yields of MSCs isolated from human tissue compartments are very low (0.001% to 0.01% of recovered nucleated cells), MSCs must be expanded in vitro for therapeutic application. But in vitro expansion results in gradual loss of their immunosuppressive potential.

The lack of maintenance of the immunosuppressive capability of MSCs limits their therapeutic application. Thus, more effective strategies to maintain the immunosuppressive potential of MSCs is needed. The mechanisms underlying MSC's immunosuppressive properties are not yet fully elucidated; however, several mediators such as Human leukocyte antigen (HLA)-G, indoleamine 2,3-dioxygenase (IDO), prostaglandin E2 (PGE2), and inducible nitric oxide synthase (iNOS) have been proposed. It has been observed that HLA-G expression in MSCs is very low and diminishes during in vitro expansion. M. Giuliani, M. Fleury, A. Vernochet, F. Ketroussi, D. Clay, B. Azzarone, J. J. Lataillade, A. Durrbach, *Long-lasting inhibitory effects of fetal liver mesenchymal stem cells on T-lymphocyte proliferation*, PLoS One 6 (2011) e19988.

Lack of sustained imunosuppression impacts the potential therapeutic application of MSCs in regenerative medicine and prevention of graft-versus-host disease. Thus, strategies to enhance and maintain MSC immunosuppressive effects would substantially improve their therapeutic utility

SUMMARY OF THE INVENTION

One object of the present invention is to provide an isolated composition of HLA-G$^+$ mesenchymal stem cells (MSCs) made by: (a) maintaining a population of mammalian tissue marrow-derived MSC for at least two passages in non-differentiating in vitro culture conditions, and (b) contacting the population of mesenchymal stem cells from step (a) with an effective amount of a DNA methylation inhibitor.

In some embodiments, the above-described composition of HLA-G$^+$ MSC is derived from mammalian adipose tissue, or bone marrow. In some embodiments, the above-described composition of HLA-G$^+$ MSC is made by a method wherein the DNA methylation inhibitor selected from a group consisting of 5-aza-2'-deoxycytidine, 5-aza-cytidine, 2-pyrimidone-1-β-D-riboside, procainamide, procaine, hydralazine and epigallocatechin-3-gallate. In some embodiments, the above-described composition of HLA-G$^+$ MSC is made by a method wherein the DNA methylation inhibitor is 5-aza-2'-deoxycytidine. In some embodiments, the HLA-G expression in the above-described composition of HLA-G$^+$ MSC can be assessed by detecting the mRNA and/or transcripts of the corresponding HLA-G isoform. In some embodiments, the HLA-G expression can be assessed by detecting the cell surface expression of the various HLA-G isoforms. In some embodiments, the above-described composition of HLA-G$^+$ MSC is made by a method wherein the population of mammalian tissue-derived MSC is maintained in non-differentiating in vitro culture conditions for at least five passages or at least ten passages. In some embodiments, at least 25% of the MSCs in the above-described composition of HLA-G$^+$ MSC express HLA-G. In some embodiments, at least 50% of the MSCs in the above-described composition of HLA-G$^+$ MSC express HLA-G. In some embodiments, at least 90% of the MSCs in the above-described composition of HLA-G$^+$ MSC express HLA-G. In some embodiments, the present application provides the above-described composition of HLA-G$^+$ MSC, wherein the HLA-G expression in the population of mammalian tissue-derived MSC treated with a DNA methylation inhibitor in step (b) is at least 10% higher than in a population of untreated MSC. In some embodiments, the present application provides the above-described composition of HLA-G$^+$ MSC, wherein the HLA-G expression in the population of mammalian tissue-derived MSC treated with a DNA methylation inhibitor in step (b) is at least 50% higher than in a population of untreated MSC. In some embodiments, the present application provides the above-described composition of HLA-G$^+$ MSC, wherein the HLA-G expression in the population of mammalian tissue-derived MSC treated with a DNA methylation inhibitor in step (b) is at least 10% higher than in a population of untreated MSC. In some embodiments, the above-described composition of HLA-G$^+$ MSC maintain the expression of HLA-G for at least two passages in non-differentiating conditions in the absence of a DNA methylation inhibitor. In some embodiments, the above-described composition of HLA-G$^+$ MSC maintain the expression of HLA-G for at least five passages in non-differentiating conditions in the absence of a DNA methylation inhibitor.

In another aspect, the present invention provides a method of generating a composition of HLA-G$^+$ mesenchymal stem cells (MSCs), the method comprising: (a) maintaining a population of mammalian tissue-derived MSC for at least two passages in non-differentiating in vitro culture conditions, and (b) contacting the population of mesenchymal stem cells from step (a) with an effective amount of a DNA methylation inhibitor.

In one aspect, the present invention provides a method of cell transplantation into a human recipient, the method comprising: (a) providing a composition of HLA-G$^+$ mesenchymal stem cells (MSCs), wherein the composition of HLA-G$^+$ mesenchymal stem cells is made by a method comprising: (i) maintaining a population of mammalian tissue-derived MSC for at least two passages in non-differentiating in vitro culture conditions, and (ii) contacting the population of mesenchymal stem cells from step (i) with an effective amount of a DNA methylation inhibitor; and (b) injecting the composition of step (a) into a human recipient. Optionally, the human recipient may suffer from a degenerative disease or the cell transplantation prevents a graft-versus-host disease.

In some embodiments, the composition of HLA-G$^+$ MSCs in the above method of cell transplantation into a human recipient express HLA-G1, and/or HLA-G3. In some embodiments the HLA-G$^+$ MSCs express HLA-G1 and HLA-G3 and do not express HLA-G5. In some embodiments of the above-described method of cell transplantation, the mammalian tissue-derived MSC is derived from adipose tissue or bone marrow tissue. In some embodiments of the above-described method of cell transplantation, the DNA methylation inhibitor contacting the population of MSCs is selected from a group comprising 5-aza-2'-deoxycytidine, 5-aza-cytidine, 2-pyrimidone-1-β-D-riboside, procainamide, procaine, hydralazine and epigallocatechin-3-gallate. In an embodiment, the DNA methylation inhibitor is 5-aza-2'-deoxycytidine. In some embodiments of the above-described method of cell transplantation, the population of mammalian tissue-derived MSC is maintained in non-differentiating in vitro culture conditions for at least five passages. In some other embodiments, the population of mammalian tissue-derived MSC is maintained in non-differentiating in vitro culture conditions for at least ten passages. In an embodiment of the above-described method of cell transplantation, at least 25% of the MSCs in the composition of HLA-G$^+$ MSCs express HLA-G. In another embodiment, at least 50% of the MSCs in the composition of HLA-G$^+$ MSCs express HLA-G. In a further embodiment, at least 90% of the MSCs in the composition of HLA-G$^+$ MSCs express HLA-G. In one embodiment, the HLA-G expression in the HLA-G$^+$ MSCs in the above-described method of cell transplantation is assessed by detecting the corresponding mRNA(s) or its transcript(s). In some embodiments of the above-described cell transplantation method, the HLA-G expression in the HLA-G$^+$ MSCs is assessed by detecting the cell surface expression of HLA-G. In some embodiments of the above-described method of cell transplantation, the HLA-G expression in the population of mammalian tissue-derived MSC treated with a DNA methylation inhibitor in step (b) is at least 10% or 50% or 100% higher than in a population of untreated MSCs. In some embodiments of the above-described cell transplantation method, the composition of the HLA-G$^+$ MSCs comprises at least about 1×10$^6$ cells per kilogram body weight of the human recipient. In some embodiments, the composition of the HLA-G$^+$ MSCs comprises at least about 2×10$^6$ cells per kilogram body weight of the human recipient. In additional embodiments of the method, the composition of the HLA-G$^+$ MSCs comprises at least about 3×10$^6$ cells per kilogram body weight of the human recipient. In still other embodiments of the method, the composition of the HLA-G$^+$ MSCs comprises at least about 4×10$^6$ cells per kilogram body weight of the human recipient. In some other embodiments of the above-described method, the composition of the HLA-G$^+$ MSCs comprises at least about 5×10$^6$ cells per kilogram body weight of the human recipient. In one embodiment of the above-described cell transplantation method, the HLA-G$^+$ MSC composition maintains the expression of HLA-G for at least two passages in non-differentiating conditions in the absence of a DNA methylation inhibitor. In other embodiments, the composition of HLA-G$^+$ MSCs maintains the expression of HLA-G for at least five passages in non-differentiating conditions in the absence of a DNA methylation inhibitor.

In one aspect, the present invention provides a composition of HLA-G$^+$ MSCs that express HLA-G1 and/or HLA-G3 but not HLA-G5, said composition being made by a method comprising (a) maintaining a population of mammalian tissue marrow-derived MSC for at least two passages in non-differentiating in vitro culture conditions, and (b) contacting the population of mesenchymal stem cells from step (a) with an effective amount of a DNA methylation inhibitor.

In another aspect, the present invention provides a method of generating a composition of HLA-G$^+$ mesenchymal stem cells (MSCs), the method comprising: (a) maintaining a population of mammalian tissue-derived MSC for at least two passages in non-differentiating in vitro culture conditions, and (b) contacting the population of mesenchymal stem cells from step (a) with an effective amount of a DNA methylation inhibitor, wherein the composition of HLA-G$^+$ MSCs express HLA-G1 and/or HLA-G3 but not HLA-G5.

A method of cell transplantation into a human recipient is also provided, the method comprising: (a) providing a composition of HLA-G$^+$ mesenchymal stem cells (MSCs) made by a method comprising: (i) maintaining a population of mammalian tissue-derived MSC for at least two passages in non-differentiating in vitro culture conditions, and (ii) contacting the population of mesenchymal stem cells from step (i) with an effective amount of a DNA methylation inhibitor; and (b) injecting the composition of step (a) into a human recipient, wherein the composition of HLA-G$^+$ MSCs express HLA-G1 and/or HLA-G3 but not HLA-G5.

In some embodiments, the invention provides a composition of HLA-G$^+$ mesenchymal stem cells (MSCs) made by: (a) maintaining a population of mammalian tissue-derived MSC for at least two passages in non-differentiating in vitro culture conditions, and (b) contacting the population of mesenchymal stem cells from step (a) with an effective amount of a DNA methylation inhibitor, wherein the said composition of HLA-G$^+$ MSCs maintain HLA-G expression for at least two passages in non-differentiating conditions in the absence of a DNA methylation inhibitor. In some embodiments, the non-differentiating condition in which the composition of HLA-G$^+$ MSCs maintain HLA-G expression in the absence of a DNA methylation inhibitor may be in vitro; in some embodiments, it can be in vivo.

In some embodiments, the HLA-G expression in the HLA-G$^+$ MSCs described above can be assessed by detecting the mRNA and/or transcripts of the corresponding HLA-G isoform. In some embodiments, the HLA-G expression can be assessed by detecting the cell surface expression of the various HLA-G isoforms.

In one embodiment, the present invention provides a composition of MSCs useful for immunosuppression applications.

In one embodiment, the DNA methylation inhibitor is 5-aza-2'-deoxycytidine (5-aza-dC).

In some embodiments, the population of mammalian tissue-derived MSC is maintained for at least five passages, or at least ten passages in non-differentiating in vitro culture conditions before treatment with a DNA methylation inhibitor.

BRIEF DESCRIPTION OF THE FIGURES

A more complete appreciation of the present invention and many of its advantages will be understood by reference to the following detailed description when considered in connection with the following drawings, which are presented for the purpose of illustration only and are not intended to be limiting, and in which.

DETAILED DESCRIPTION OF THE INVENTION

The following explanations of terms and examples are provided to better describe the present compounds, compositions and methods, and to guide those of ordinary skill in the art in the practice of the present disclosure. It is also to be understood that the terminology used in the disclosure is for the purpose of describing particular embodiments and examples only, and is not intended to be limiting.

Described herein are methods of enhancing the immunosuppressive capability of mesenchymal stem cells comprising contacting the mesenchymal stem cells with an effective amount of an agent that modulates HLA-G expression. In one aspect, the present invention provides a composition of HLA-G$^+$ mammalian mesenchymal stem cells (MSC), wherein the mammalian mesenchymal stem cells are maintained for at least two passages in non-differentiating in vitro culture conditions, and then contacted with an effective amount of a DNA methylation inhibitor. Also provided is a method of generating a composition of HLA-G$^+$ mesenchymal stem cells (MSC), the method comprising maintaining a population of mammalian tissue-derived MSC for at least two passages in non-differentiating in vitro culture conditions, and then contacting the population of mesenchymal stem cells with an effective amount of a DNA methylation inhibitor. In another aspect, the present invention provides a method of cell transplantation into a human recipient, by first contacting a population of mammalian tissue-derived mesenchymal stem cells maintained in non-differentiating in vitro conditions for at least two passages with an effective amount of DNA methylation inhibitor, and then injecting the treated mesenchymal stem cells into a human being.

In one embodiment, the DNA methylation inhibitor is 5-aza-dC. In another embodiment, the mammalian tissue-derived MSC is derived from adipose tissue or bone marrow. Optionally, the human recipient transplanted with the composition of HLA-G$^+$ MSC described herein, may suffer from a degenerative disease or the cell transplantation prevents a graft-versus-host disease.

Definitions

As used herein, "immunosuppression" refers to an immune response to an allogeneic or xenogeneic graft that is smaller than the immune response that would be generally observed in an animal. Immunosuppressive events are well-known to those skilled in the art, often resulting in an extension of graft survival time. Such effects may also alternatively be referred to in the art as immunotoleragenic effect. Thus, in one aspect the invention provides methods and compositions for inducing tolerance to a donor cell, tissue or organ in a recipient individual. Immunosuppressive effects include but are not limited to impact on NK cell killing, migration, and cell viability, proliferation and IFNγ production, regulation of cytokine production in blood mononuclear cells and cytotoxic T lymphocytes (CTLs), suppression of CTL killing and viability, inhibition of proliferation and induction of a suppressive phenotype in T-helper cells, and alteration of dendritic cell stimulatory capacity. Immunosuppression may also be achieved by binding of HLA-G to suitable receptors. The major receptors for HLA-G on leukocytes are the leukocyte-inhibitory receptors (LILRB), formerly known as the immunoglobulin-like transcript (ILT) receptors. LILRBs are expressed by T and B lymphocytes and also by NK cells and mononuclear phagocytes, and LILRBs abrogate activating signals received by these cells.

As used herein, the term mesenchymal stem cell (MSC) refers to a cell capable of giving rise to differentiated cells in multiple mesenchymal lineages, including osteoblasts, adipocytes, myoblasts, chondroblasts, and fibroblasts. The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human. Generally, mesenchymal stem cells also have one or more of the following properties: an ability to undergo asynchronous, or asymmetric replication, that is where the two daughter cells after division can have different phenotypes; extensive self-renewal capacity; and clonal regeneration of the tissue in which they exist, for example, the non-hematopoietic cells of bone marrow.

MSC may be characterized by both the presence of cell surface markers associated with specific epitopes identified by antibodies and the absence of certain cell surface markers as identified by the lack of binding of specific antibodies. MSC may also be identified by functional assays both in vitro and in vivo, particularly assays relating to the ability of stem cells to give rise to multiple differentiated progeny, assays for responsiveness to canonical WNT signaling, and the like.

Human MSCs have been previously characterized as expressing a number of cell-surface proteins, including CD54, CD9, CD29, CD44, CD56, CD61, CD63, CD71, CD73, CD90, CD97, CD98, CD99, CD105, CD106, CD112, CD146, CD155, CD166, CD276, and CD304. Human MSCs are often characterized by the cell-surface expression of CD29, CD44, CD73, CD90, and CD105, and the absence of cell-surface expression of hematopoietic markers CD34 and CD45. Thus, the invention provides for a new sub-population of MSCs that lack or have low CD54 cell-surface expression. This sub-population of MSCs allow for enhanced or superior differentiation of MSCs into different cell-lineages, such as osteoblasts, chondrocytes, and adipocytes.

MSCs can be obtained from bone marrow using standard procedures known in the art. For example, bone marrow aspirates can be collected from consenting healthy donors. A person of skill in the art will know of various methods that can be used to isolate human MSCs (hMSCs). For example, see Aggarwal & Pittenger, (2005), *Human mesenchymal stem cells modulate allogeneic immune cell responses*, Blood, 105: 1815-1822. Generally, mononuclear cells are isolated from bone marrow aspirates by gradient centrifugation. Mononuclear cells are then seeded into flasks containing MSC medium, such as Dulbecco's modified Eagle medium (DMEM)-low glucose supplemented with 10 mM L-glutamine and 10% fetal calf serum (FCS). hMSC cultures are then grown at 37° C. under a humidified 5% $CO_2$ atmosphere. Nonadherent cells are removed after 24 hours (h) by washing with PBS-HSA solution. The medium is changed every 4 days and after 2 weeks the cultures should be mostly confluent. hMSCs are recovered using trypsin and replated as passage 1 cells. Subsequently cells can be kept in culture for at least up to 8 passages and tested routinely for the presence of MSC-associated surface molecules. Under such conditions, hMSCs maintain their multilineage capacity to differentiate into osteoblasts, chondrocytes, and adipocytes.

MSCs have been harvested from the supportive stroma of a variety of tissues. For example, in both mouse and human, a candidate population of cells has been identified in subcutaneous adipose tissue. These cells have demonstrated the same in vitro differentiation capacity as bone marrow-derived mesenchymal stem cells for the mesenchymal lineages, such as osteoblasts, chondrocytes, myocytes, neurons, and adipocytes (Zuk et al. (2002) Mol. Bioi. Cell, 13, 4279-95; Fujimura et al. (2005) Biochem. Biophys. Res. Commun., 333, 116-21). Additionally, cell surface antigen profiling of these cells has revealed similar cell surface marker characteristics as the more widely studied bone-marrow derived MSCs (Simmons et al. (1994) Prog. Clin. Biol. Res. 389, 271-80; and Gronthos et al. (2001) J. Cell Physiol. 189, 54-63). An exemplary protocol for obtaining MSCs from adipose is provided in the Examples later.

"HLA-G" is a major histocompatibility antigen, and is key to immune function and transplantation rejection. Features important to the function of this molecule include a low number of functionally different alleles; seven alternatively spliced transcripts, four encoding membrane bound proteins and three encoding soluble proteins; and the generation of proteins with a truncated cytoplasmic tail, revealing a cryptic retrieval motif that may interfere with presentation of exogenous peptides.

In HLA-G, nine polymorphisms have been identified in the exons encoding the extracellular domain, and one in the 3' untranslated region. Of the nine, five result in amino acid differences and four do not. One major deletion has been identified: a single base pair (bp) deletion at nucleotide 1597, which causes a frameshift at amino acid 130. This deletion of a cytosine residue at codon 130 results in a null allele (called G*0105N), which does not encode functional HLA-G1 or HLA-G5 protein isoforms.

The full-length isoform, HLA-G1, is structurally similar to other class I genes, except for the truncated cytoplasmic tail. The G2 isoform results from the removal of exon 3; the resulting heavy chain cannot form heterodimers with β2 microglobulin and homodimerizes to form an HLA class-II-like structure. HLA-G1 and HLA-G2 are also expressed as soluble proteins (called HLA-G5 and HLA-G6, respectively) because of the inclusion of intron 4 sequences in the mature mRNA. HLA-G5 and HLA-G6 secreted proteins include a unique sequence of 21 amino acids. HLA-G5 may or may not associate with β2m, whereas HLA-G6 does not. HLA-G3 results from the removal of exons 3 and 4. HLA-G4 and HLA-G7 mRNAs are scarce in placentas, and the functions of their protein products remain unknown. The soluble HLA-G isoforms circulate in mothers' blood throughout pregnancy. Soluble HLA-G is also produced by some but not by all preimplantation embryos.

As used herein, the term HLA-G refers to any one of the seven alternatively spliced transcripts and gene products (e.g., intracellular protein, cell surface marker, soluble protein) of the human HLA-G locus, including any of the polymorphisms at this locus, e.g. G*0105N. The full length isoform, HLA-G1, is listed in Genbank at accession number NM_002127, and the protein at accession NP_002118.1. The G2 isoform lacks exon 3. The G3 isoform lacks exons 3 and 4. HLA-G5 and HLA-G6 are soluble forms of HLA-G1 and HLA-G2, which include intron 4 sequences encoding a unique 21 amino acid. HLA-G3 results from the removal of exons 3 and 4.

The genome locus for HLA-G may be accessed at Genbank, accession NG_002398, and is referenced in Robinson and Marsh (2000) Rev. Immunogenet. 2 (4), 518-531; Beck and Trowsdale (2000) Annu. Rev. Genomics Hum. Genet. 1, 117-137; Rhodes and Trowsdale (1999) Rev. Immunogenet. 1 (1), 21-31; and Trowsdale (1993) Trends Genet. 9 (4), 117-122.

References relating to the sequence of HLA-G, each of which are herein specifically incorporated by reference particularly for the teaching of HLA-G sequences, include Yie et al. (2006) Hum. Reprod. 21 (10), 2538-2544; Cirulli et al. (2006) Diabetes 55 (5), 1214-1222; Hviid et al. (2006) Sarcoidosis Vase Diffuse Lung Dis 23 (1), 30-37; Hviid et al. (2006) Hum. Immunol. 67 (1-2), 53-62; Ishitani et al. (1992) Proc. Natl. Acad. Sci. U.S.A. 89 (9), 3947-3951; Pook et al. (1991) Hum. Immunol. 32 (2), 102-109; Zemmour et al. (1991) Hum. Immunol. 31.

The term "effective amount" is an amount sufficient to produce a desired effect, e.g., an amount sufficient to alter the protein expression profile of HLA-G of mesenchymal stem cells.

As used herein, "methylation" is a chemical or biochemical process of introducing a methyl group into an organic molecule, in this case, the DNA. In biological systems, DNA methylation can serve as a mechanism for changing the structure of DNA without altering its coding function or its sequence. DNA methylation is a heritable, reversible and epigenetic change. It can alter gene expression, particularly by inactivating genes, which has profound developmental and disease consequences.

The mammalian genome contains approximately $3 \times 10^7$ 5-methylcytosine ($m^5C$) residues, all or most at 5'-$m^5$CpG-3'. About 60% of CpG sites are methylated in the DNA of somatic cells. Methylation recruits a variety of transcriptional repressors, including histone deacetylases and other proteins that cause chromosome condensation and silencing. While it has long been known that methylation of a promoter causes profound silencing if the sequence is rich in CpG dinucleotides, only recently have genetic and biochemical experiments begun to identify the biological functions of DNA methylation after many years of controversy and speculation. For example, if a maternally-inherited copy of a gene is more highly methylated than the paternally-inherited copy, the paternally-inherited copy will be expressed more effectively. Similarly, when a gene is expressed in a tissue-specific manner, that gene often will be unmethylated in the tissues where it is active but highly methylated in the tissues where it is inactive.

Epigenetic alterations are found in nearly all types of cancer, and involve methylation of the DNA sequence, rather than changes to the sequence itself. The most studied form of epigenetic alteration is CpG dinucleotide methylation.

"DNA methylation inhibitors" are a class of compounds or mixture of compounds that reduce, prevent, reverse or inhibit the methylation of DNA. In some embodiments, DNA methylation inhibitors of the present invention have the ability to inhibit DNA methylation by inhibiting DNA methyltransferases. For example, the compounds of the present invention may inhibit DNA methylation as a result of inhibiting the activity of DNA methyltransferase 1 (DNMT1)

"DNA methyltransferases" (DMT) are a family of enzymes that promote the covalent addition of a methyl group to a specific nucleotide base in a molecule of DNA.

All the known DNA methyltransferases use S-adenosyl methionine (SAM) as the methyl donor. Four active DNA methyltransferases have been identified in mammals. They are named DNMT1, DNMT2, DNMT3A and DNMT3B.

DNMT1 is the most abundant DNA methyltransferase in mammalian cells and considered to be the key maintenance methyltransferase in mammals. It predominantly methylates hemimethylated CpG di-nucleotides in the mammalian genome and is responsible for maintaining methylation patterns established in development. The enzyme is about 1620 amino acids long, the first 1100 amino acids constituting the regulatory domain, and the remaining residues constituting the catalytic domain. These are joined by Gly-Lys repeats. Both domains are required for the catalytic function of DNMT1.

DNMT3 is a family of DNA methyltransferases that can methylate hemimethylated and unmethylated CpG at the same rate. The architecture of DNMT3 enzymes is similar to DNMT1 with a regulatory region attached to a catalytic domain.

Examples of DNA Methylation Inhibitors

In one embodiment, the DNA methylation inhibitor is a methyltransferase inhibitor. For example, the DNA methyltransferase inhibitor may be selected from cytosine analogues such as 5-aza-2'-deoxycytidine (also known as decitabine), 5-aza-cytidine (also known as azacitidine), and 1-(β-D-ribofuranosyl)-1,2-dihydropyrimidin-2-one or 2-pyrimidone-1-β-D-riboside (also known as zebularine). While not wishing to base the method or the practice of it on any particular theory or set of theories, the inventors recognize that these compounds' ability to inhibit DNA methylation arises, at least partly, out of their ability to inhibit DNA methyltransferase.

In one preferred embodiment, the DNA methylation inhibitor is 5-aza-2'-deoxycytidine (5-aza-dC). 5-aza-2'-deoxycytidine or decitabine is the compound 4-amino-1-(2-deoxy-b-D-erythro-pentofuranosyl)-1,3,5-triazin-2(1H)-one, the structure of which is shown below.

Without being bound by any particular theory, this pyrimidine analog of cytdine gets incorporated into DNA and is known to form covalent complexes with DMTs, leading to depletion of active enzymes (Fenaux P, (2005) Nature Clinical Practice, 2, S36-44).

In another embodiment, the DNA methyltransferase inhibitor is 5-aza-C or azacitidine (trade name Vidaza), which is the compound 4-amino-1-β-D-ribofuranosyl-s-triazin-2(1H)-one, the structure of which is shown below.

In cells, 5-aza-C can be converted to 5-aza-dC by the enzyme ribonucleotide reductase. These pyrimidine analogues of cytidine incorporate into RNA and DNA respectively, and form covalent complexes with DNMTs, leading to depletion of active enzymes (Fenaux P, (2005) Nature Clinical Practice, 2, S36-44).

In another embodiment, the DNA methylation inhibitor is zebularine, also known as 1-(β-D-ribofuranosyl)-1,2-dihydropyrimidin-2-one or 2-pyrimidone-1-β-D-riboside, the structure of which is shown below.

DNA methylation inhibitors may also include non-nucleoside analogues such as procainamide, procaine, hydralazine and epigallocatechin-3-gallate (EGCG).

Procainamide (trade names Pronestyl, Procan, Procanbid) is the compound 4-amino-N-(2-diethylaminoethyl)benzamide, the structure of which is shown below.

Without being bound by theory, procainamide has been shown to inhibit DNA methyltransferase activity and reactivate silenced gene expression in cancer cells by reversing CpG island hypermethylation. Procainamide specifically inhibits the hemimethylase activity of DNA methyltransferase 1 (DNMT1), the mammalian enzyme thought to be responsible for maintaining DNA methylation patterns during replication.

Procaine is the compound 2-(diethylamino)ethyl-4-aminobenzoate, the structure of which is shown below.

Without being bound by theory, procaine is a DNA-demethylating agent that is understood to inhibit DNA methyltransferases by interfering with enzyme activity.

Hydralazine (Apresoline) is the compound 1-hydrazinophthalazine monohydrochloride, the structure of which is shown below.

Another example of DNA methylation inhibitor is EGCG, which is understood to inhibit DNMT activity and reactivate methylation-silenced DNA. Epigallocatechin-3-gallate (EGCG) is a catechin analogue having the structure shown below.

In another embodiment, the DNA methyltransferase inhibitor is RG108, also known as N-phthalyl-1-tryptophan, the structure of which is shown below.

RG108 is a DNA methyltransferase inhibitor that is understood to inhibit DNA methyltransferases by interfering with enzyme activity.

In one embodiment, an appropriate combination of different methylation inhibitors can be used to achieve the desired level of inhibition.

HLA-G Expression in MSCs

In one aspect, the invention provides a method of up-regulating HLA-G expression in mammalian tissue-derived MSCs maintained for certain number of passages in non-differentiation in vitro conditions by exposing MSCs to a methylation inhibitor and measuring the HLA-G up-regulation by comparing the RNA expression of the treated cells with the untreated cells. In some embodiments, the HLA-G expression is enhanced 2-5 fold in the treated cells in comparison to the untreated cells.

In some embodiments, the methylation modulating agent is administered to the mesenchymal stem cells in vitro, ex vivo, and/or in vivo (i.e., administration to a subject having the mesenchymal stem cells).

The amount of the methylation inhibitor needed to achieve the desired level of methylation inhibition, and HLA-G upregulation would depend upon the agent and the cells. In one embodiment, a population of MSCs is contacted with a methylation inhibitor such that the final concentration of the agent is about 10 µM. In other embodiments, the final concentration of the methylation inhibitor is about 0.1 µM to about 1 µM, or about 1 µM to about 10 µM, or about 10 µM to about 100 µM. In one preferred embodiment, 5-aza-2'-deoxycytidine is administered to a population of MSCs, at a final concentration of about 10 µM.

Different methylation modulating agents, or different treatments with the same agent, or different cell lines, may yield different levels of methylation reduction. In some embodiments, the methylation level is reduced by at least 5% upon treatment with an agent; in other embodiments, it is reduced by at least 10%, by at least 15%, by at least 20%, by at least 25%, by at least 30%, by at least 40%, or by at least 50% compared to an untreated sample. Particularly effective methylation inhibitors, or agents used in particularly susceptible systems may yield even greater reduction levels, for instance at least 60%, 70%, 80%, 90%, or in some examples 95% or more.

In some embodiments, the HLA-G expression is enhanced by at least at least 5% upon treatment with an agent; in other embodiments it is enhanced by at least 10%, by at least 15%, by at least 20%, by at least 25%, by at least 30%, by at least 40%, by at least 50%, by at least 60%, by at least 70%, by at least 80%, or by at least 90% compared to an untreated sample. Particularly effective methylation inhibitors, or agents used in particularly susceptible systems, may yield even greater upregulation of HLA-G levels, for instance by at least 2 fold, by at least 3 fold, by at least 4 fold, by at least 5 fold, by at least 6 fold, by at least 7 fold, by at least 8 fold, by at least 9 fold, or by at least 10 fold compared to the untreated cells.

One skilled in the art would understand that there are various ways that the expression level of HLA-G can be assessed in the MSCs. In one preferred embodiment, the HLA-G expression can be assessed by determining the level of HLA-G mRNA or its transcript. Thus, a cDNA reverse transcribed from an mRNA, an RNA transcribed from that cDNA, a DNA amplified from the cDNA, an RNA transcribed from the amplified DNA, which are all derived from the mRNA transcript and detection of such derived products may be indicative of the presence and/or abundance of the original transcript in a sample. In some embodiments, the upregulation of the various isoforms of HLA-G can be detected by the upregulation of transcripts of the corresponding mRNA. Various techniques can be used to determine the expression level of HLA-G, which may include RT-PCR, Northern blots and Western blots.

Similarly, other methods of assessing the expression of HLA-G in the composition of HLA-G$^+$ MSCs can also be used, including detecting cell surface expression of the various isoforms of HLA-G. In some embodiments, the HLA-G$^+$ MSCs are identified and/or isolated by binding to the cell with reagents specific for the cell surface markers of interest. In some embodiments, the reagents specific for the cell surface markers of interest are antibodies, which may be directly or indirectly labeled. Such antibodies will usually include antibodies specific for HLA-G, for example, antibodies specific for HLA-G1, or HLA-G3. Further enrichment for the desired cell type may be obtained by selection for cell surface markers characteristic of the cells, e.g. by flow cytometry, magnetic bead separation, panning, etc., as known in the art.

Analysis or separation by cell staining may use conventional methods known in the art. Techniques providing accurate enumeration include confocal microscopy, fluorescence microscopy, fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, polynucleotide probes specific for an mRNA of interest, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

In some embodiments, the MSCs are maintained in vitro under non-differentiating conditions for a certain number of passages before they are treated with an agent that modulates the expression of HLA-G. In some embodiments, the mesenchymal stem cells have been cultured for at least 1 passage; in other embodiments they are cultured for at least 2 passages, for at least 3 passages, for at least 4 passages, for at least 5 passages, for at least 6 passages, for at least 7 passages, for at least 8 passages, for at least 9 passages, and for at least 10 passages, before they are treated with a DNA-methylation inhibitor. In some embodiments, the MSCs have been cultured for at least 15 passages, or at least 20 passages before they are contacted with a DNA-methylation inhibitor.

In some embodiments, at least 5% of the MSCs in the composition of HLA-G$^+$ MSCs prepared by the method described herein express HLA-G or show an up-regulation of HLA-G. In some embodiments, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the MSCs in the composition of HLA-G+ MSCs prepared by the method described herein express HLA-G or show an up-regulation of HLA-G.

In some embodiments, the present invention provides an isolated composition of HLA-G+ MSCs that express HLA-G1 and HLA-G3, and do not express HLA-G5 by the methods described herein. For example, the present invention provides HLA-G+ MSCs that express HLA-G1 and HLA-G3 and not HLA-G5, the said composition being made by a method comprising (a) maintaining a population of mammalian tissue marrow-derived MSC for at least two passages in non-differentiating in vitro culture conditions, and (b) contacting the population of mesenchymal stem cells from step (a) with an effective amount of a DNA methylation inhibitor. In some embodiments, the mesenchymal stem cells have been cultured in non-differentiating in vitro conditions for at least 1 passage, at least 2 passages, at least 3 passages, at least 4 passages, at least 5 passages, at least 6 passages, at least 7 passages, at least 8 passages, at least 9 passages, at least 10 passages, at least 15 passages or at least 20 passages before they are treated with a DNA-methylation inhibitor.

In other embodiments, the present invention provides a method of generating a composition of HLA-G+ mesenchymal stem cells (MSC), the method comprising: (a) maintaining a population of mammalian tissue-derived MSC for at least two passages in non-differentiating in vitro culture conditions, and (b) contacting the population of mesenchymal stem cells from step (a) with an effective amount of a DNA methylation inhibitor, wherein the composition of HLA-G+ MSCs that express HLA-G1 and HLA-G3 and not HLA-G5. In some embodiments, the mesenchymal stem cells have been cultured in non-differentiating in vitro conditions for at least 1 passage, at least 2 passages, at least 3 passages, at least 4 passages, at least 5 passages, at least 6 passages, at least 7 passages, at least 8 passages, at least 9 passages, at least 10 passages, at least 15 passages or at least 20 passages before they are treated with a DNA-methylation inhibitor.

Treatment with DNA methylation inhibitor can also result in epigenetic regulation of HLA-G in the HLA-G+ MSCs made by the methods described herein. Epigenetic changes alter gene expression, and are heritable and yet do not arise due to alterations of DNA sequence. Epigenetic differences initiated in a cell by DNA methylation inhibitors may be sustained through several passages of cell division. The present invention also provides a method modulating epigenetic control of HLA-G expression in MSCs. In some embodiments, the invention provides a composition of of HLA-G+ mesenchymal stem cells (MSC) made by: (a) maintaining a population of mammalian tissue marrow-derived MSC for at least two passages in non-differentiating in vitro culture conditions, and (b) contacting the population of mesenchymal stem cells from step (a) with an effective amount of a DNA methylation inhibitor, wherein the said composition of HLA-G+ MSC maintains enhanced HLA-G expression for at least two passages, at least three passages, at least four passages, at least five passages, at least six passages, at least seven passages, at least eight passages, at least nine passages or at least ten passages in the absence of a DNA methylation inhibitor.

Transplanting into a Human Recipient

In one aspect, the present invention provides a method of injecting a human recipient with a composition of HLA-G+ MSCs prepared by the methods described in this invention.

In one embodiment, the present invention provides a method of cell transplantation of HLG+ MSCs into a human recipient, wherein the said HLA-G+ MSCs are made by maintaining a population of mammalian tissue-derived mesenchymal stem cells in non-differentiating in vitro conditions for at least two passages, and then treating with an effective amount of DNA methylation inhibitor. In some embodiments, the composition of HLA-G+ MSCs used in cell transplantation as described herein express HLA-G1 and/or HLA-G3 but not HLA-G5. As already discussed in this application, the types and quantities of DNA methylation inhibitors used, the amount of HLA-G upregulation, and the percentage of cells showing HLA-G upregulation may vary. Similarly, as already discussed, the mammalian tissue-derived MSCs can be maintained in non-differentiating in vitro conditions for at least 2 passages, for at least 3 passages, for at least 4 passages, for at least 5 passages, for at least 6 passages, for at least 7 passages, for at least 8 passages, for at least 9 passages, for at least 10 passages, for at least 15 passages, or for at least 20 passages before contacting the MSCs with a DNA methylation inhibitor.

In some embodiments, the composition of HLA-G+ MSC injected into a human recipient comprises at least about $1 \times 10^6$ cells, at least about $2 \times 10^6$ cells, at least about $3 \times 10^6$ cells, at least about $4 \times 10^6$ cells, at least about $5 \times 10^6$ cells, at least about $6 \times 10^6$ cells, at least about $7 \times 10^6$ cells, at least about $8 \times 10^6$ cells, at least about $9 \times 10^6$ cells, or at least about $10 \times 10^6$ cells per kg body weight of the human recipient.

Thus, in one embodiment of the invention, a human recipient is injected with a population of mesenchymal stem cells after they have been treated with an effective amount of DNA methylation inhibitor, 5-aza-dC. In some embodiments, the composition comprising the HLA-G expressing MSCs comprise other cells, tissues, excipients, and bioactive materials suitable for the treatment of a particular disease. In some embodiments, the invention provides pharmaceutical compositions comprising the HLA-G expressing MSCs formulated in a pharmaceutically acceptable carrier. The composition of cells can also be provided on a cell growth matrix such as hydrogels.

In one embodiment, the methylation inhibitors are administered to mesenchymal stem cells in vivo. In still another embodiment, the methylation inhibitors are administered before, during and after the injection of MSCs into a recipient. The mesenchymal cells and/or the methylation inhibitors may be administered on a regular basis or schedule including but not limited to daily, weekly, biweekly, or monthly. The methylation inhibitor may be 5-aza-dC or it could be selected from any of the other methyltransferase inhibitors described in this invention or any other DNA methylation inhibitor known in the art.

Optionally, the recipient of MSC transplantation may be suffering from a disease that could benefit from such transplantation. Disorders or diseases that may be treated or prevented by administering the compositions of human cells of the present invention include diseases that can be treated or prevented by suppressing immune responses. Thus, disorders or diseases that can be treated or prevented by the present composition include the autoimmune disorder, inflammatory disease, a degenerative disease and graft-versus-host disease.

Examples of autoimmune disorders that may be treated or prevented by the present compositions include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre syndrome, Hashimoto's thyroiditis, idiopathic pulmonary fibrosis, idiopathic thrombocytopenia purpura (ITP), irritable bowel disease (IBD), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, stiff-man syndrome, systemic lupus erythematosus, lupus erythematosus, takayasu arteritis, temporal arteristis, giant cell arteritis, ulcerative colitis, uveitis, vitiligo and Wegener's granulomatosis. Preferably autoimmune disorders that may be treated or prevented by the present compositions include rheumatoid arthritis, type 1 diabetes mellitus, multiple sclerosis, systemic lupus erythematosus, and atopy.

A degenerative disease is a disease in which the function or structure of the affected tissues or organs will progressively deteriorate over time. Examples of degenerative diseases that can be treated with the present invention include Amyotrophic Lateral Sclerosis (ALS), Alzheimer's disease, Parkinson's Disease, Multiple system atrophy, Niemann Pick disease, Atherosclerosis, Progressive supranuclear palsy, Tay-Sachs Disease, Diabetes, Heart Disease, Keratoconus, Inflammatory Bowel Disease (IBD), Prostatitis, Osteoarthritis, Osteoporosis, Rheumatoid Arthritis, Huntington's Disease, Chronic traumatic encephalopathy, Epilepsy, Dementia, Renal failure, Multiple sclerosis, Malaria with CNS degeneration, Neuro-AIDS, Lysosomal storage diseases, Encephalatis of viral, bacterial or autoimmune origin.

The mesenchymal stem cell compositions of the invention are useful for suppressing graft rejection immune responses in the transplanted tissues, organs or cells.

Based on the standard clinical and laboratory experiments and methods, an ordinary person skilled in the art can easily select a subject in need of injection of the HLA-G$^+$ MSCs prepared by the methods described in this invention.

EXAMPLES

Isolation of Adipose-Derived MSCs (AMSCs)

AMSCs were isolated from adult human lipoaspirate of patients undergoing liposuction procedure. Briefly, abdominal subcutaneous adipose samples were washed with Hanks' balanced salt solutions (HBSS) (Invitrogen, Carlsbad, CA). After gentle shaking, the lower phase (containing stem cells, adipocytes, and blood) was washed and enzymatically dissociated with 0.075% collagenase type I (Sigma-Aldrich, St. Louis, MO)/HBSS for 1 h at 37° C. with gentle shaking. Collagenase was inactivated by adding fetal bovine serum (FBS) and samples were centrifuged at 400 g for 10 min at 25° C. The pellet was resuspended in RBC lysis buffer (eBioscience, San Diego, CA) and adherent cell masses were removed by sequential passing through 100, 70, and 40 µm mesh filters. Cells were then added into equal amounts of HISTOPAQUE-1077 (Sigma) and centrifuged at 400 g for 30 min to separate MSCs. Cells were seeded at $1-2 \times 10^4$ cells/cm$^2$ and grown in Dulbecco's modified eagle medium (DMEM, Invitrogen) supplemented with 10% FBS and 1% penicillin/streptomycin (Invitrogen) at 37° C. in a humidified 5% CO$_2$ incubator and media changed every 2-3 d. After reaching 70-80% confluence, cells were washed with phosphate buffered saline (PBS), detached with 0.25% trypsin-EDTA (Invitrogen), then centrifuged and expanded at 1:3 split ratios.

Culturing of Bone Marrow-Derived MSCs (BMSCs)

Adult BMSCs (passage 2) were obtained from Cell Applications, Inc. (San Diego, CA) and cultured in alpha-minimum essential medium (α-MEM) (Invitrogen) supplemented with 10% FBS and 1% penicillin/streptomycin (Invitrogen) at 37° C. in a humidified 5% CO$_2$ incubator. At 70-80% confluence, cells were harvested with 0.25% trypsin-EDTA (Invitrogen) and expanded at 1:3 split ratios.

Cell Lines

JEG-3 (ATCC, Manassas, VA) is a choriocarcinoma cell line and was maintained in Eagle's minimum essential medium with Earl's balanced salt solution (ATCC) and 10% FBS at 37° C. in a humidified 5% CO$_2$ incubator. K562 cells (ATCC) were maintained in Iscove's modified Dulbecco's medium (ATCC) supplemented with 10% FBS. JEG-3 and K562 cells were used as positive and negative controls for HLA-G expression, respectively.

Immunophenotyping

MSCs were harvested and expression of surface markers was characterized with flow cytometry. Briefly, cells ($1 \times 10^5$) were collected, washed with PBS, and blocked for 30 min with 10% goat serum/3% BSA diluted in PBS. Cells were washed (3×) with cold PBS and incubated with 1:100 dilution of mouse anti-human CD105, CD73, CD34, and CD45 (all from BioLegend, San Diego, CA) and CD90 (Becton-Dickinson, San Jose, CA) for 60 min on ice. Isotype-matched control antibodies were used to evaluate non-specific binding. After 3 washes with cold PBS, cells were incubated with allophycocyanin (APC) labeled goat anti-mouse IgG secondary antibody (abcam, Cambridge, MA) for 30 min, followed by 3 washes with PBS. Cells were resuspended in PBS and 10,000 events were acquired with a FACScantoII flow cytometer (BD) and results were analyzed using cyflogic software (CyFlo Ltd, Finland).

Adipogenic and Osteogenic Differentiation

Adipogenic and osteogenic differentiation was induced. Briefly, to induce adipogenic differentiation, MSCs were seeded at $1 \times 10^4$ cells/cm$^2$ in growth medium and allowed to reach 70-80% confluence. Medium was supplemented with 0.5 mM 3-isobutyl-methylxanthine (IBMX) (Sigma), 1 µM dexamethasone (Sigma), 10 µM insulin (Santa Cruz Biotechnology, Santa Cruz, CA), and 100 µM indomethacin (Santa Cruz Biotechnology). Medium was replaced every 3 to 4 d for 14 d and fat vacuoles stained with Oil Red-O solution. To induce osteogenic differentiation, MSCs were seeded at $2.5 \times 10^3$ cells/cm$^2$ in growth medium and allowed to reach 50% confluence. Growth medium was supplemented with 10 mM β-glycerophosphate, 0.1 μM dexamethasone, and 0.2 mM ascorbic acid-2-phosphate (all from Sigma) and induction medium replaced every 3-4 d. After 21 d, mineral deposition was visualized by staining with Alizarin Red (Sigma).

Demethylating Treatments

Demethylating treatment was carried out by culturing MSCs for 72 h with 5-aza-2'-deoxycytidine (5-aza-dC) (Sigma) at a final concentration of 10 μM or with the solvent DMSO as control.

RNA Isolation and RT-PCR

After 72 h treatment, cells were trypsinized and total RNA extracted using RNeasy kit (Qiagen, Valencia, CA) according to the manufacturer's protocol. Semi-quantitative RT-PCR reactions were performed on a DNA Engine Peltier Thermal Cycler (Bio-Rad, Hercules, CA) as previously described. M. D. Nicola, et al., *Human bone marrow stromal cells suppress T-lymphocyte proliferation induced by cellular or non-specific mitogenic stimuli*, Blood 99: 3838-3843 (2002). Briefly, first strand cDNA was synthesized in 50 μl reactions from 2 μg total RNA using oligo dT primers and TaqMan reverse transcription reagents (Applied Biosystems, Foster City, CA). Reverse transcription (RT) reactions were carried out at 24° C. for 10 min, 48° C. for 1 h, and heat inactivation at 95° C. for 5 min. RT samples were diluted at 1:4 in DNase, RNase free water and PCR performed in 20 μl reaction using Taq PCR master mix (Qiagen), 1 μl of diluted template, and HLA-G primers (Table 1). β-actin was used as an internal control. PCR program consisted of 94° C. for 4 min, followed by 30 cycles at 94° C. for 30 s, 60° C. for 1 min, and 72° C. for 1 min with a final extension at 72° C. for 10 min. PCR products were separated using 1.5% agarose gel in the presence of 0.5 μg/ml ethidium bromide and imaged using the FluorChem® HD2 Imaging System (Alpha Innotech Corporation, San Leandro, CA). Densitometry analysis was performed using AlphaEase FC software (Alpha Innotech Corporation). Relative expression levels were calculated from the ratio of integrated density values of HLA-G to that of β-actin.

TABLE 1

Primers used for HLA-G gene expression analysis in MSCs.

| Gene | | Primer sequence (5'-3') | Reference ID | Tm (° C.) | Amplicon Size (bp) |
|---|---|---|---|---|---|
| HLA-G1 | F | CCAATGTGGCTGAACAA AGG | NM_002127.4 | 60 | 426 |
| | R | AGG GAA GAC TGC TTC CAT CTC | | | |
| HLA-G3 | F | AGCGAGGCCAAGCAGTC TTC | NM_002127.4 | 60 | 167 |
| | R | GCGAGATCTTCACATTG CAGCCTGAGA | | | |
| HLA-G5 | F | ATA CCT GGA GAA CGG GAA GG | NM_002127.4 | 60 | 363 |
| | R | AGG CTC CTG CTT TCC CTA AC | | | |

TABLE 1-continued

Primers used for HLA-G gene expression analysis in MSCs.

| Gene | | Primer sequence (5'-3') | Reference ID | Tm (° C.) | Amplicon Size (bp) |
|---|---|---|---|---|---|
| ACTB | F | TCTACAATGAGCTGCGT GTG | PMID: 22732094 | 60 | 231 |
| | R | CGTAGATGGGCACAGTG T | | | |

Statistical Analysis

All data are expressed as means±SEM (standard error of the mean) of 3 independent experiments. Statistically significant differences were evaluated with two-tailed student T-test with $p<0.05$ considered significant.

Results

Phenotypic Characterization

Figure 1:
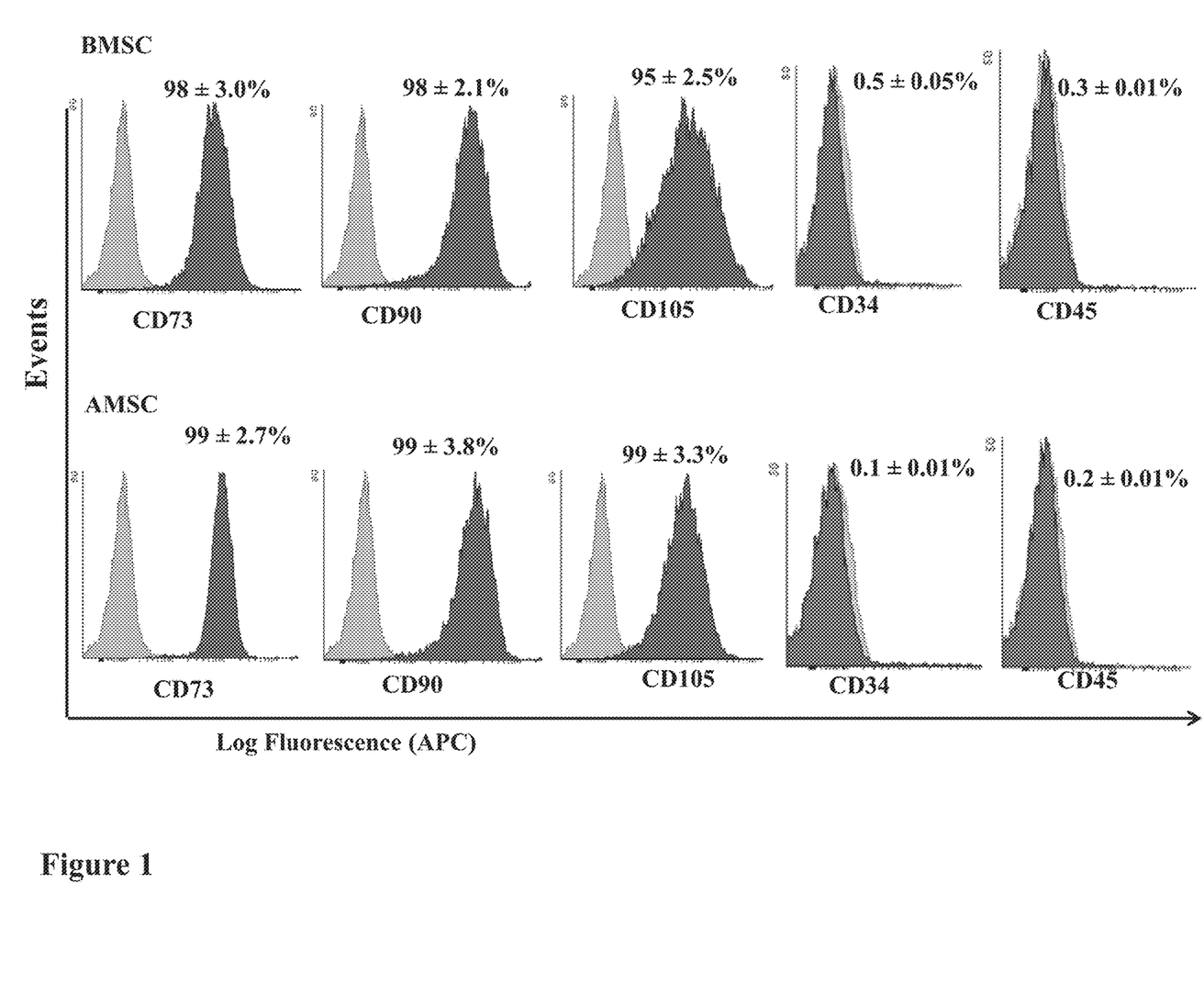
FIG. 1 shows a flow cytometry analysis of surface markers of adipose-derived MSCs (AMSCs) and bone marrow-derived MSCs (BMSCs). MSCs were characterized for cell surface marker expression using flow cytometry. Specific markers are presented as dark histograms and isotype-matched control antibodies as gray histograms. Representative histograms from 3 independent runs are shown.
Figure 2A:
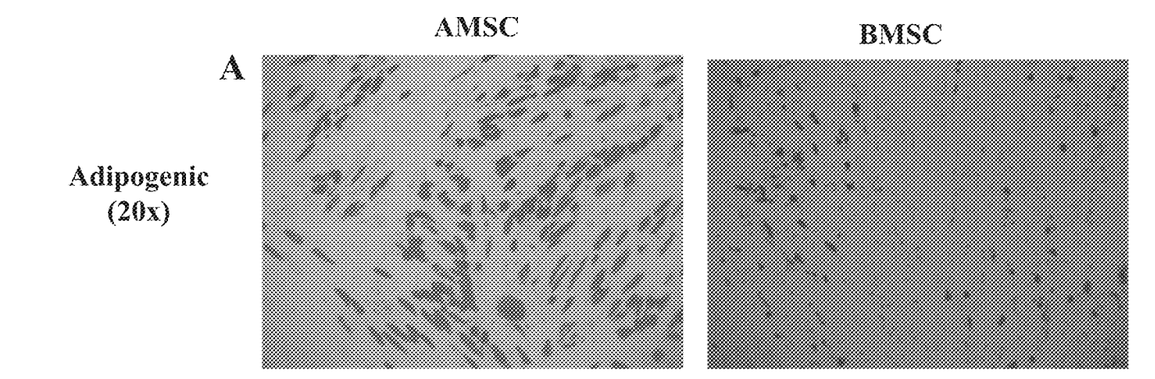
FIGS. 2A-2B display the adipogenic and osteogenic differentiation of AMSCs and BMSCs visualized by staining with Alizarin Red (Sigma).
Figure 2B:
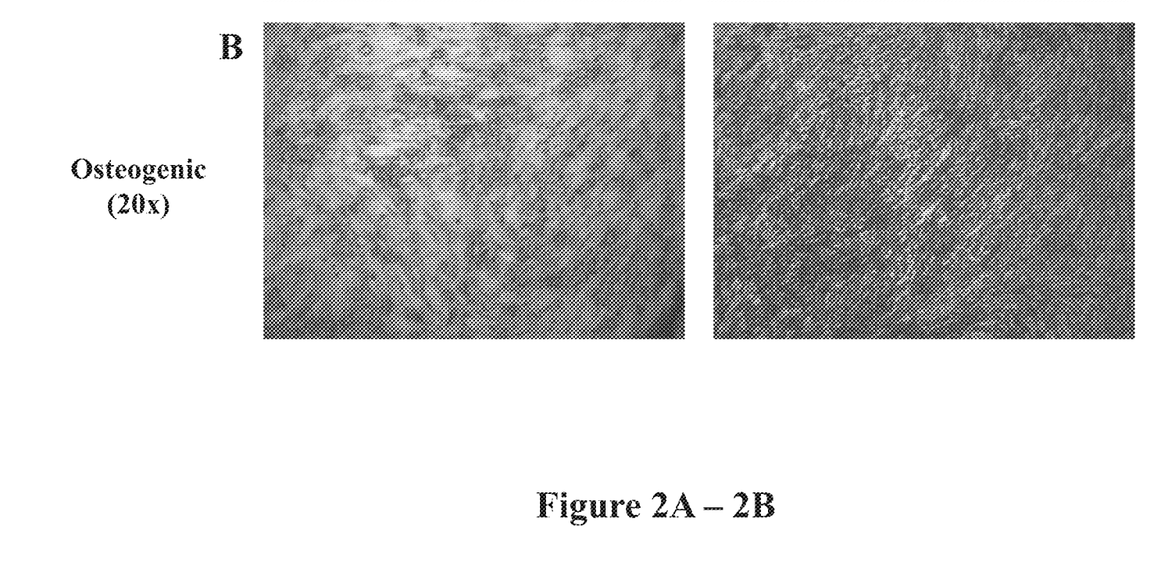

Flow cytometry analysis of MSCs revealed that both AMSCs and BMSCs were strongly positive for CD105, CD73 and CD90, but negative for hematopoietic markers CD34 and CD45 (FIG. 1). MSCs treated with adipogenic and osteogenic media differentiated into adipocytes and osteocytes, respectively (FIG. 2). Hence, both AMSCs and BMSCs fulfilled the 3 proposed criteria to define MSCs. M. D. Nicola, et al., *Human bone marrow stromal cells suppress T-lymphocyte proliferation induced by cellular or non-specific mitogenic stimuli*, Blood 99: 3838-3843 (2002).

Inhibition of DNA Methylation Upregulates MSC HLA-G1 and -G3 Transcription

Figure 3A:
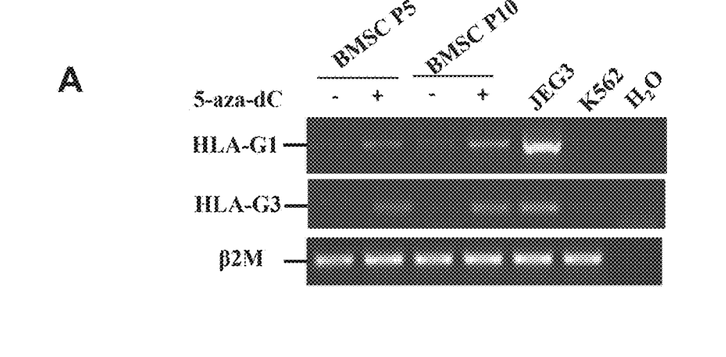
FIG. 3A shows the HLA-G1 and HLA-G3 expression in 5-aza-dC treated BMSC relative to untreated BMSC at passage 5 (P5) and passage 10 (P10). HLA-G expression was determined by analyzing RT-PCR products on 1.5% agarose gel. β-actin was used as an internal control. JEG-3 and K562 cells were used as positive and negative controls for HLA-G expression, respectively.
Figure 3B:
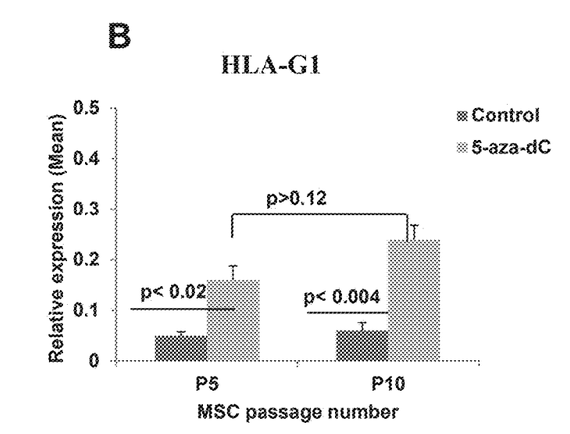
FIG. 3B shows the relative HLA-G1 expression in 5-aza-dC treated P5 and P10 BMSCs in comparison to untreated cells.
Figure 3C:
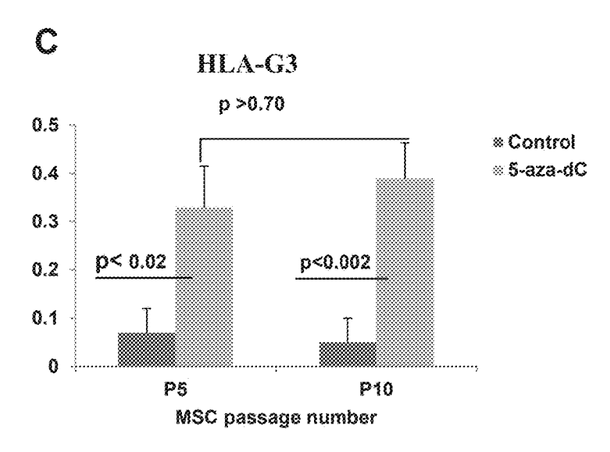
FIG. 3C shows the relative HLA-G3 expression in 5-aza-dC treated P5 and P10 BMSCs in comparison to untreated cells.

MSCs that had been maintained for 5 passages (P5) and 10 passages (P10) in non-differentiating in vitro conditions were exposed to 5-aza-dC (a known DNA methyltransferase inhibitor) at 10 μM for 72 h. Total RNA was extracted from both treated and untreated cells, and HLA-G1 and -G3 transcripts analyzed by semi-quantitative RT-PCR. Relative HLA-G1 expression in 5-aza-dC treated P5 (0.16±0.01) and P10 BMSCs (0.24±0.01) was statistically significantly higher than untreated P5 (0.04±0.007, $p<0.02$) and P10 (0.06±0.01, $p<0.004$) cells, respectively (FIGS. 3A & 3B). No significant difference of HLA-G1 expression ($p>0.12$) between P5 and P10 was observed (FIG. 3B). Relative HLA-G3 expression in treated P5 (0.33±0.08) and P10 (0.38±0.07) BMSCs was statistically significantly higher than untreated P5 (0.07±0.01, $p<0.02$) and P10 (0.05±0.01, $p<0.07$) cells, respectively (FIGS. 3A & 3C). No significant difference of HLA-G3 expression ($p>0.70$) between P5 and P10 was observed (FIG. 3C).

Figure 4A:
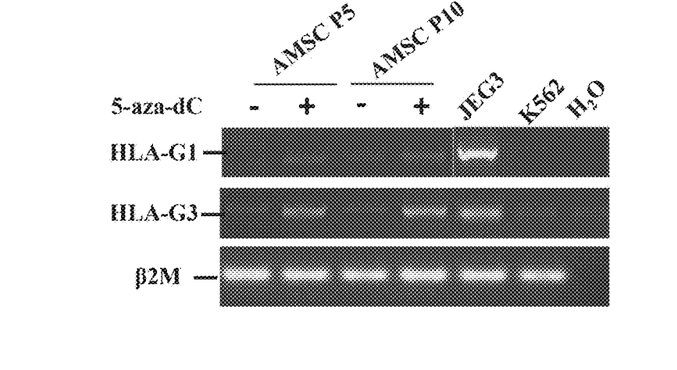
FIG. 4A shows the HLA-G1 and HLA-G3 expression in 5-aza-dC treated AMSC relative to untreated AMSC at passage 5 (P5) and passage 10 (P10). HLA-G expression was determined by analyzing RT-PCR products on 1.5% agarose gel. β-actin was used as an internal control. JEG-3 and K562 cells were used as positive and negative controls for HLA-G expression, respectively.
Figures 4B, 4C:
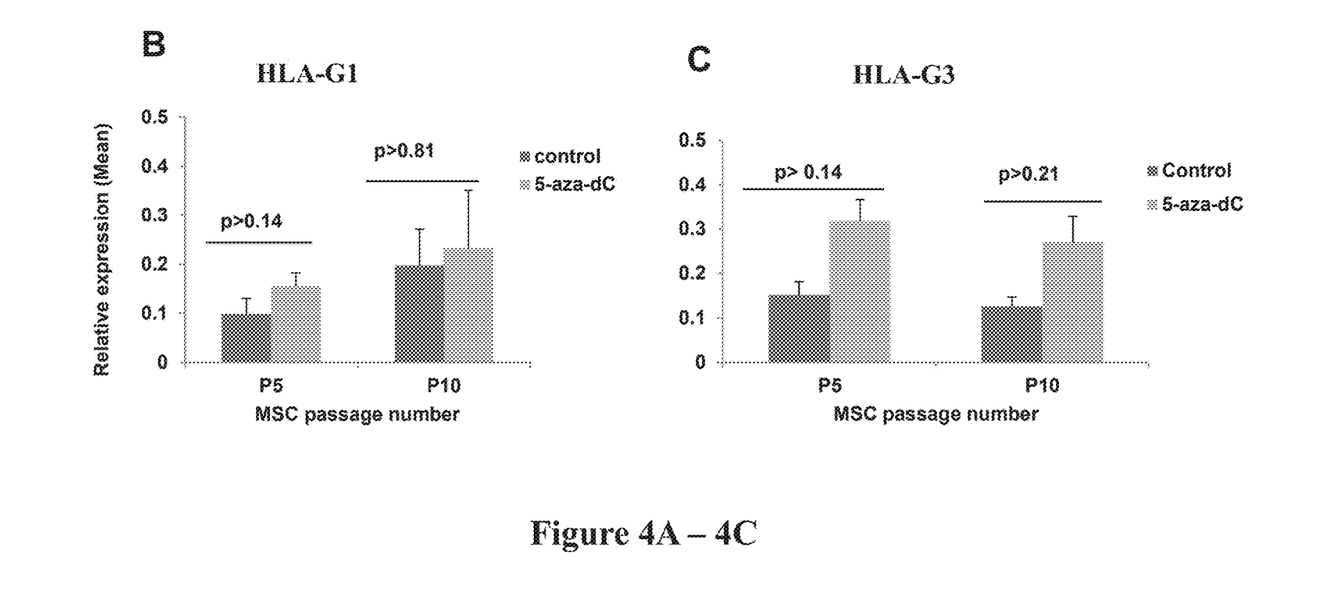
FIG. 4B shows the relative HLA-G1 expression in 5-aza-dC treated P5 and P10 AMSCs in comparison to untreated cells.
FIG. 4C shows the relative HLA-G3 expression in 5-aza-dC treated P5 and P10 AMSCs in comparison to untreated cells.

Although the difference was not significant, relative HLA-G1 expression in treated P5 (0.15±0.02, $p>0.14$) and P10 (0.23±0.19, $p>0.81$) AMSCs was higher than untreated P5 (0.09±0.03) and P10 (0.19±0.07) AMSCs, respectively (FIGS. 4A & 4B). Relative HLA-G3 expression in treated P5 (0.31±0.05) and P10 (0.27±0.06) AMSCs was ~2-fold higher than untreated P5 (0.15±0.03) and P10 (0.13±0.03) AMSCs, respectively (FIGS. 4A & 4C).

HDAC Inhibition Does Not Modify HLA-G Expression

Figure 5A:
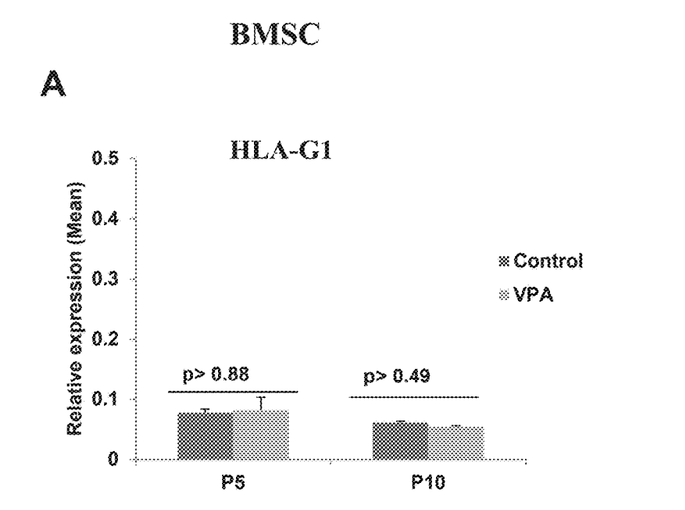
FIG. 5A provides a bar graph of HLA-G1 expression in valproic acid (VPA) treated BMSC relative to untreated BMSC. Relative expression levels as measured by RT-PCR were obtained by dividing the expression of HLA-G transcript to that of endogenous reference β2M gene. HLA-G1 expression in BMSCs at passage 5 (P5) and passage 10 (P10) were studied.
Figure 5B:
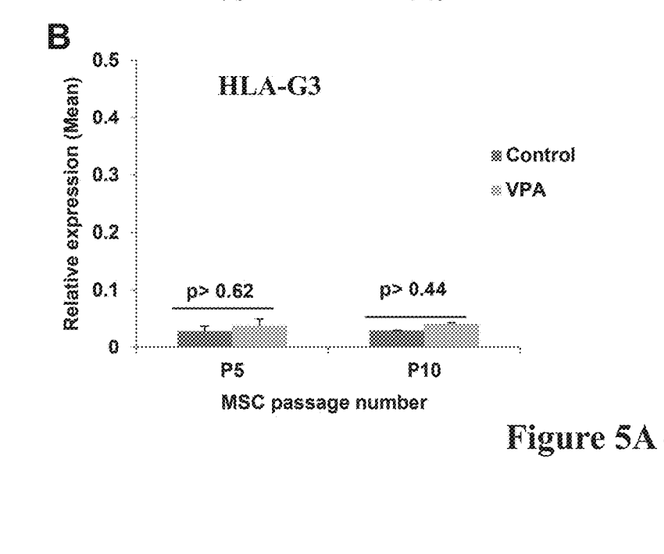
FIG. 5B shows the relative HLA-G3 expression in VPA treated P5 and P10 BMSCs in comparison to untreated cells.
Figure 5C:
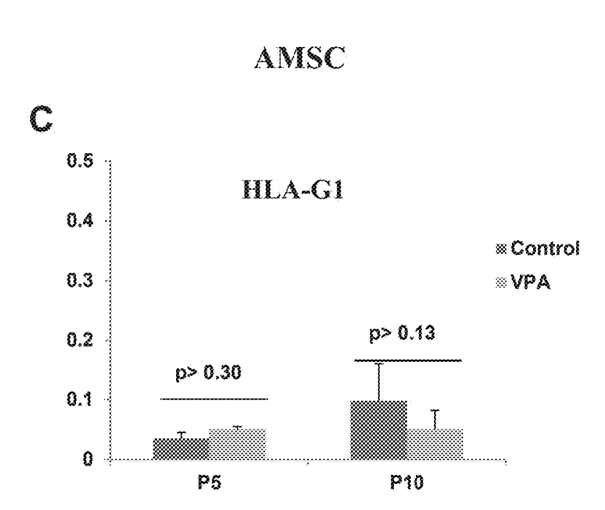
FIG. 5C shows the relative HLA-G1 expression in VPA treated P5 and P10 AMSCs in comparison to untreated cells.
Figure 5D:
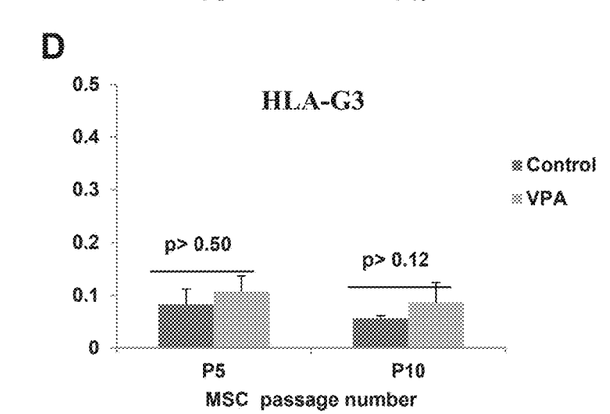
FIG. 5D shows the relative HLA-G3 expression in VPA treated P5 and P10 AMSCs in comparison to untreated cells.

MSCs were treated with Valproic acid (VPA) (a known histone deacetylase inhibitor (HDAC) inhibitor) and HLA-G1, -G3 and HLA-G5 transcripts were evaluated by semi-quantitative RT-PCR. Relative HLA-G1 expression in VPA treated P5 (0.08±0.02) and P10 BMSCs (0.05±0.002) was not statistically significantly different from untreated P5 (0.07±0.002, p>0.88) and P10 (0.06±0.002 p>0.49) cells, respectively (FIG. 5A). Relative HLA-G3 expression in treated P5 (0.04±0.01) and P10 (0.01±0.001) BMSCs was not statistically significantly different from untreated P5 (0.03±0.008, p>0.62) and P10 (0.02±0.001, p>0.44) cells, respectively (FIG. 5B). Similarly, there was no upregulation of HLA-G1 (FIG. 5C), HLA-G3 (FIG. 5D), or HLA-G5 (Table 2) mRNA in AMSCs treated with VPA.

HLA-G5 mRNA level was evaluated with RT-PCR. Results of relative expression of HLA-G5 level were obtained by dividing band intensity values of HLA-G5 to that of endogenous reference $\beta 2M$ gene. Means±SEM from 3 independent runs are illustrated in Table 2.

TABLE 2

Effects of 5-aza-dC and VPA on HLA-G5 expression in MSCs

| Treatment Groups | BMSCs | AMSCs |
| --- | --- | --- |
| Untreated Control | 0.007 ± 0.0001 | 0.006 ± 0.00 |
| 5-aza-dC | 0.009 ± 0.00 | 0.009 ± 0.001 |
| VPA | 0.006 ± 0.004 | 0.006 ± 0.00 |

The present invention demonstrated that HLA-G expression could be enhanced in late passage mammalian tissue-derived MSCs by affecting the methylation status of DNA. This invention shows that exposure to DNA demethylating agents like 5-aza-dC result in an upregulation of HLA-G in mesenchymal stem cells. These findings provide the basis for improving the immunoregulatory capabilities of MSCs used for transplantation and treatment of degenerative diseases and graft-versus-host diseases.

Those skilled in the art would readily appreciate that all parameters and examples described herein are meant to be exemplary and that actual parameters and examples will depend upon the specific application for which the composition and methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that the invention may be practiced otherwise than as specifically described. Accordingly, those skilled in the art would recognize that the use of a composition or method in the examples should not be limited as such. The present invention is directed to each individual composition, or method described herein. In addition, any combination of two or more such compositions or methods, if such composition or methods are not mutually inconsistent, is included within the scope of the present invention.

I claim:

1. A method of transplanting a composition comprising a population of mesenchymal stem cells (MSCs), the method comprising injecting the composition into a human recipient, wherein the population of MSCs comprises MSCs that express HLA-G (HLA-G+ MSCs), wherein the population of MSCs was contacted with a DNA methylation inhibitor prior to the injection, and wherein the HLA-G+ MSCs have (a) a methylation level at least 5% lower than MSCs that have not been contacted with the DNA methylation inhibitor and (b) HLA-G expression at least 10% higher than MSCs that have not been contacted with the DNA methylation inhibitor.

2. The method of claim 1, wherein the HLA-G+ MSCs express HLA-G1.

3. The method of claim 1, wherein the HLA-G+ MSCs are derived from adipose tissue or bone marrow.

4. The method of claim 1, wherein the population of MSCs comprises at least 25% HLA-G+ MSCs.

5. The method of claim 1, wherein the HLA-G expression in the HLA-G+ MSCs is assessable by detecting a corresponding mRNA or its transcript.

6. The method of claim 1, wherein the HLA-G expression in the HLA-G+ MSCs is assessable by detecting a cell surface expression of HLA-G.

7. The method of claim 4, wherein the population of MSCs comprises at least 50% HLA-G+ MSCs.

8. The method of claim 7, wherein the population of MSCs comprises at least 90% HLA-G+ MSCs.

9. The method of claim 1, wherein the human recipient has a disease and wherein the disease is treated or prevented by suppressing the human recipient's immune response.

10. The method of claim 9, wherein the disease is an autoimmune disorder, an inflammatory disease, a degenerative disease, or a graft-versus-host disease.

11. The method of claim 1, wherein the HLA-G+ MSCs express HLA-G3.

12. The method of claim 1, wherein the HLA-G+ MSCs express HLA-G1 and HLA-G3.

13. The method of claim 12, wherein the HLA-G+ MSCs do not express HLA-G5.

* * * * *